United States Patent [19]

Watanabe et al.

[11] 4,074,042
[45] Feb. 14, 1978

[54] PSEUDO-ISOCYTIDINE

[75] Inventors: Kyoichi Aloisius Watanabe; Chung Kwang Chu, both of Portchester; Jack Jay Fox, White Plains, all of N.Y.

[73] Assignee: Research Corporation, New York, N.Y.

[21] Appl. No.: 602,692

[22] Filed: Aug. 7, 1975

[51] Int. Cl.² .............................................. C07H 7/06
[52] U.S. Cl. ...................................... 536/1; 424/180; 536/18
[58] Field of Search ........... 260/209 R, 210 R, 234 R, 260/211.5 R; 536/1, 115, 18, 55

[56] References Cited

U.S. PATENT DOCUMENTS

| | | | |
|---|---|---|---|
| 3,480,613 | 11/1969 | Walton | 260/209 R |
| 3,674,774 | 7/1972 | Williams et al. | 260/210 AB |
| 3,755,293 | 8/1973 | Shirato et al. | 260/209 R |

OTHER PUBLICATIONS

Cohn, "The Journal of Biological Chemistry", vol. 235, No. 5, May, 1960, pp. 1488–1497.
Shapiro, "Jour. Amer. Chem. Soc.", vol. 83, 1961, pp. 3920–3921.

*Primary Examiner*—Johnnie R. Brown
*Attorney, Agent, or Firm*—Omri M. Behr

[57] ABSTRACT

Pseudo-isocytidine is disclosed as well as methods and intermediates useful in its preparation. The novel compound pseudo-isocytidine, preferably the beta-anomer thereof, is an active cytostatic and anti-leukemic agent.

15 Claims, No Drawings

PSEUDO-ISOCYTIDINE

The invention described herein was made in the course of work under a grant from the Department of Health, Education and Welfare.

BACKGROUND OF THE INVENTION

Several nucleosides are now known which contain a carbon to carbon linkage between the sugar and aglycon portion of the molecule. Examples of such "pseudo" compounds include pseudouridine (5-(beta-D-ribofuranosyl)uracil, Shapiro et al., J.Am.Chem.-Soc., 83, 3920 (1961) and pseudocytidine, Michelson et al., Biochemistry 1, 490 (1962).

DESCRIPTION OF THE INVENTION

The present invention relates to the novel compound pseudo-isocytidine and the acid addition salts thereof. A further aspect of the present invention relates to a process for preparing pseudo-isocytidine and intermediates useful therein.

Pseudo-isocytidine is readily obtained by a multi-step process starting from the known 2,3-O-lower alkylidene-5-O-trityl-D-ribofuranoses. A preferred starting material is 2,3-O-isopropylidene-5-O-trityl-D-ribofuranose.

In a first reaction step the aforesaid ribofuranose starting material is alkylated with (carb-lower alkoxymethylene)triphenylphosphorane so as to produce lower alkyl 2-(2,3-O-lower alkylidene-5-O-trityl-D-ribofuranosyl)acetate. This alkylation reaction is conveniently carried out in an inert, polar organic solvent such as acetonitrile at an elevated temperature, preferably at the reflux temperature of the reaction mixture. In a preferred embodiment the lower alkoxy radical of the alkylation reagent is ethoxy and the resulting intermediate obtained is the ethyl ester, i.e., ethyl 2-(2,3-O-isopropylidene-5-O-trityl-D-ribofuranosyl)acetate.

The above intermediate is then formylated with a lower alkyl formate and an alkali metal hydride in anhydrous ether containing a small amount of a lower alkanol to yield a lower alkyl 2-formyl-2-(2,3-O-lower alkylidene-5-O-trityl-D-ribofuranosyl)acetate alkali metal enolate. The reaction is preferably carried out at room temperature for a period of 15 to 24 hours. The lower alkyl utilized in the formate reagent will also be reflected in the lower alkanol selected. Thus in a preferred embodiment ethyl formate is used as the formylating agent and ethanol is thus employed as the lower alkanol. Sodium hydride is the alkali hydride of choice in this reaction. A preferred intermediate thus produced is ethyl 2-formyl-2-(2,3-O-isopropylidene-5-O-trityl-D-ribofuranosyl)acetate sodium enolate.

The aforesaid alkali metal enolate, which may be utilized in crude form, is then reacted with guanidine preferably as an acid addition salt, i.e., the hydrochloride in the presence of base such as lower alkanolic alkali metal lower alkoxide at elevated temperatures, preferably at the reflux temperature of the reaction mixture, to thus produce 5-(2,3-O-lower alkylidene-5-O-trityl-D-ribofuranosyl)-isocytidine in primarily the alpha-anomer form. Removal of byproducts can readily be accomplished by column chromatography, e.g., over silica gel. The resulting syrupy crude product can be treated with reflux lower alkanol, preferably methanol to crystallize out the alpha-anomer in pure form. However, it is preferably to utilize the crude syrup for further transformation as it contains the desired beta-anomer.

In a preferred embodiment of the above process step the lower alkanolic alkali metal lower alkoxide employed is ethanolic sodium ethoxide.

The crude alpha-beta mixed anomers from the above reaction step is then treated with a lower alkanolic mineral acid, e.g., 10% methanolic hydrogen chloride at a temperature in the range of 15° to 25° C., preferably at room temperature to effect cleavage of the lower alkylidene and trityl protecting groups. The product which precipitates out from this reaction mixture is pseudo-isocytidine (beta-anomer). The alpha-anomer is found in the filtrate and can be isomerized to the beta-anomer after isolation by solvent evaporation utilizing the aforesaid lower alkanolic mineral acid treatment. Product pseudo-isocytidine is obtained as the mineral acid addition salt which crystallizes from solution.

In an alternative process aspect, the above described lower alkyl 2-formyl-2-(2,3-O-lower alkylidene-5-O-trityl-D-ribofuranosyl)acetate alkali metal enolate is reacted with a diazo-lower alkane, e.g., diazomethane at a temperature in the range of 15° to 25° C., preferably at room temperature in an inert organic solvent such as an ether, preferably ethyl ether. The product lower alkyl 2-loweralkoxymethylene-2-(2,3-O-loweralkylidene-5-O-trityl-D-ribofuranosyl)acetate can then be reacted with guanidine as described above to produce the pseudo-isocytidine of the present invention.

Psuedo-isocytidine forms acid addition salts with both organic and inorganic acids. Preferable acid addition salts are the pharmaceutically acceptable acid addition salts. Non-pharmaceutically acceptable acid addition salts can be converted to the pharmaceutically acceptable acid addition salts by ion-exchange techniques well known in the art. Examples of pharmaceutically acceptable acid addition salts include hydrochloric acid, hydrobromic acid, sulfuric acid, phosphoric acid, citric acid, acetic acid, succinic acid, maleic acid, methanesulfonic acid, p-toluenesulfonic acid and the like.

Pseudo-isocytidine and its acid addition salts are useful therapeutic agents and may be employed in the form of pharmaceutical preparations which contain them in association with a compatible pharmaceutical carrier which can be an organic or inorganic inert carrier material suitable for enteral or parenteral administration such as, for example, water, gelatin, gum arabic, lactose, starches, magnesium stearate, talc, vegetable oils, polyalkylene glycols, petroleum jelly, etc. The pharmaceutical preparations can be made up in solid form (e.g., as tablets, dragees, suppositories or capsules) or in liquid form (e.g., as solutions, suspensions or emulsions). The preparations may be sterilized and/or may contain adjuvants such as preserving, stabilizing, wetting or emulsifying agents, salts for varying the osmotic pressure or buffers. Such preparations may also contain other therapeutic agents.

The compounds of the present invention, and most especially the beta-anomer of pseudo-isocytidine and salts thereof, are valuable therapeutic agents exhibiting utility as cytostatic agents, anti-leukemia agents and anti-viral agents.

Thus pseudo-isocytidine (beta-anomer) in an in vitro test against leukemia L5178Y cells shows a 50% inhibition of growth at 0.8 μg/ml. whereas the known anti-leukemic agent 5-azacytidine in the same test requires 1.0 μg/ml. to achieve 50% inhibition of growth.

Additional in vitro test results with other leukemic cell strains are summarized below in Table I.

TABLE I

| Compound | P815 | L1210 | 50's (µg/ml) L5178Y/ARA-C | P815/ARA-C | SKL-7 |
|---|---|---|---|---|---|
| Pseudo-isocytidine | 0.5 | 0.5 | 2.6 | 0.04 | 0.9 |
| 5-azacytidine | 1.9 | 0.6 | 4.0 | 0.5 | 2.1 |

Activity has also been demonstrated for pseudo-isocytidine (beta-anomer) in an in vivo test in the mouse against the arabinosylcytosine resistant mouse leukemia P815/ARA-C. On a dosage schedule of 60 mg/kg of pseudo-isocytidine i.p. daily for four days there was a mean survival of 22.8 days. In comparison control mice had a mean survival of 9.3 days and mice treated with 5 mg/kg of 5-azacytidine daily for four days had a mean survival of 19.5 days.

Similar results have been observed in mice with pseudo-isocytidine against leukemia L1210/Mtx (40 mg/kg daily × 10) gave 14.7 days mean survival vs. 8.3 days mean survival for controls) and in mouse leukemia L1210/0 (40 mg. q.d. × 5d = 21.1 days mean survival vs. 9.5 days mean survival for controls).

A pharmaceutical preparation in dosage unit form of pseudo-isocytidine (beta-anomer) can expediently contain approximately 250 mg. to about 2000 mg., preferably from 500 mg. to 1000 mg. of the compound for administration by parenteral modes.

The term "lower alkylidene" as used herein is meant to include a straight or branched chain saturated hydrocarbon radical covalently bonded to two atoms other than hydrogen through one carbon atom of the radical and having from 1 to 7 carbon atoms, preferably from 2 to 4 carbon atoms. Suitable lower alkylidene groups include ethylidene, isopropylidene and i-butylidene. The isopropylidene radical is the lower alkylidene of preference.

The term "lower alkoxy" as used herein is meant to include a lower alkyloxy radical wherein lower alkyl is a straight or branched chain saturated hydrocarbon radical having from 1 to 7 carbon atoms, preferably 1 to 4 carbon atoms. Examples of suitable lower alkoxy radicals include methoxy, ethoxy, t-butoxy, etc. Ethoxy is the lower alkoxy of preference. Similarly, lower alkyl radicals include methyl, ethyl, i-propyl, n-butyl, n-hexyl and the like. The term "alkali metal" is meant to include lithium, sodium, potassium, rubidium and cesium. Sodium is the alkali metal of preference. The term "lower alkanol" is meant to include alcohols having from 1 to 7 carbon atoms, preferably 1 to 4 carbon atoms such as methanol, ethanol, isopropanol, n-butanol, n-hexanol and the like.

EXAMPLE 1

2,3-O-isopropylidene-5-O-trityl-D-ribofuranose (43.2 g., 0.1 mole) and (carbethoxymethylene) triphenylphosphorane (37.3 g., 0.11 mole) were dissolved in dry acetonitrile (500 ml., dried over 4A molecular sieves) and the solution was heated under reflux for 4 hours. The solvent was removed in vacuo and the residue was dissolved in ether (~500 ml.). On cooling the solution in an ice bath, triphenylphosphine oxide precipitated which was removed by filtration and the filtrate was evaporated to dryness. This procedure was repeated 3 times to remove most of triphenylphosphine oxide. The yield of the crude product ethyl 2-(2,3-O-isopropylidene-5-O-trityl-D-ribofuranosyl)acetate was 45 g. This crude material is suitable for further transformation but can be further purified if desired by silica gel column chromatography using benzene-ether (10:1) as the eluent.

EXAMPLE 2

A mixture of ethyl formate (10 g. distilled over $K_2CO_3$), ethyl 2-(2,3-O-isopropylidene-5-O-trityl-D-ribofuranosyl)-acetate (50.2 g., 0.1 mole), anhydrous ether (100 ml., distilled over $LiAlH_4$) and absolute ethanol (8 ml.) was added dropwise over a period of about 1 hour to a suspension of NaH (5 g, 0.1 mole, 50% in mineral oil) in anhydrous ether (~150 ml.) containing 2 ml. of absolute ethanol. (2 ml. of ethanol was added to ~150 ml. of anhydrous ether just prior to the addition of the mixture of starting material and ethyl formate in ether). The miture was stirred overnight at room temperature. The solvent and the excess ethyl formate was removed by evaporation in vacuo at room temperature (25°). The residue consisting of 55.2 g. of crude ethyl 2-formyl-2-(2,3-O-isopropylidene-5-O-trityl-D-ribofuranosyl)-acetate sodium enolate was not purified further, but used directly in the next step.

EXAMPLE 3

The sodium enolate, obtained in Example 2 (55.2 g. crude) was suspended in water (500 ml.), and the suspension was neutralized with 80% HOAc, then extracted with ether (500 ml. × 2). The ether extracts were washed with water, dried ($Na_2SO_4$) and the ether was evaporated to near dryness below 20°. To the residue was added diazomethane (generated from 25 g. of N-methyl-N'-nitroso-N-nitrosoguanidine in 200 ml. of ether). The mixture was left overnight at room temperature, then evaporated to a brown syrup comprising crude product ethyl 2-methoxymethylidine-2-(2,3-O-isopropylidene-5-O-trityl-D-ribofuranosyl)-acetate.

EXAMPLE 4

Guanidine HCl (15.0 g.) was added to ethanolic sodium ethoxide (prepared by dissolving 4.6 g. of Na in 200 ml. of absolute ethanol) and the mixture was stirred for 10 min. at room temperature, then the mixture was added to a solution of 55.2 g. of the crude enolate prepared in Example 2 in absolute ethanol (100 ml). The reaction mixture was heatted under reflux for 24 hours., cooled in an ice bath, and carefully neutralized with 1N HCl (to pH 6.8~7). During the addition of 1N HCl, a small amount of product precipitated. Water was added to complete precipitation. The supernatant was decanted and the residual brown syrup was dissolved in benzene (~100 ml.), dried ($Na_2SO_4$) and chromatographed on a column of silica gel G (~700 g.) using benzene-ether (30:1) as the eluent to remove all the unknown by-products. 1 L fractions were collected and each fraction was checked by tlc. Finally, the column was washed with benzene-MeOH (19:1). The crude syrup (~7 g.), which was obtained after evaporation of the solvent, was taken into methanol and the mixture was refluxed for 10 min. White crystals started to form. (caution: bumping!!). After cooling, the crystals (2.7 g.)

were filtered off to yield 5-(2,3-O-isopropylidene-5-O-trityl-D-ribofuranosyl)-isocytosine as the alpha-anomer in analytically pure form. m.p. 251°–253°.

Microanalysis ($C_{31}H_{31}N_3O_5$). Calcd. C, 70.86; H, 5.90; H, 8.00; Found: C, 70.85; H, 5.81; N, 7.78.

UV $\lambda_{max}$
(ethanol) 291 nm
(pH 12) 277 nm
(pH 1) 259 nm

EXAMPLE 5

The crude syrup (~7 g.) comprising 5-(2,3-O-isopropylidene-5-O-trityl-D-ribofuranosyl)-isocytosine mixed anomers was dissolved in 50 ml. of 10% methanolic hydrogen chloride, and the mixture was stirred overnight at room temperature. The crystals precipitated (pseudo-isocytidine .HCl 760 mg.) was filtered and the filtrate (containing alpha-anomer) was evaporated to dryness. The residue was partitioned between ether (75 ml.) and water (75 ml.). The aqueous layer was washed with ether (50 ml.) and evaporated to dryness. The residue (after several co-evaporations with ethanol to remove traces of water) was dissolved in 30 ml. of 10% methanolic hydrogen chloride. During the next two weeks, 430 mg. of pseudo-isocytidine .HCl crystallized out.

beta-anomer .HCl: mp 215-216° (dec.)
$[\alpha]_D^{25}D+120$ (c 0.1, water)
uv$\lambda_{max}$pH 1 262 ($\epsilon$ 7,800)
$\lambda_{max}$pH 7 288 ($\epsilon$ 5,700)
$\lambda_{max}$pH 12 277 ($\epsilon$ 7,340)
pKa 3.72 ± 0.05 and 8.97 ± 0.05 alpha-anomer .HCl: mp 182°–183° (dec).
$[\alpha]_D^{25}-164°$(c 0.1, water)
$\lambda_{max}$pH 1 262 ($\epsilon$7,470)
$\lambda_{max}$pH 7 290 ($\epsilon$3,890) and 270 (3,980)
$\lambda_{max}$pH 12 277 ($\epsilon$7,170)
pKa 3.92 ± 0.05 and 9.12 ± 0.05.

Analysis ($C_9H_{14}ClN_3O_5$): Calcd. C, 38.64; H, 5.02; H, 15.02; Cl, 12.70; Found: C, 38.81; H, 5.12; N, 14.88; Cl, 12.91

Analysis ($C_9H_{14}ClN_3O_5$): Calcd. C, 38.74; H, 5.10; N, 14.91; Cl, 12.82

EXAMPLE 6

In analogy to Examples 4 and 5, the product of Example 3, ethyl-2-methoxy methylidene 2-(2,3-O-isopropylidene-5-O-trityl-D-ribofuranozyl)acetate, is converted to pseudo-isocytidine hydrochloride.

We claim:

1. Pseudo-isocytidine and pharmaceutically acceptable acid addition salts thereof.

2. The compound of claim 1 is pseudo-isocytidine beta-anomer.

3. The compound of claim 1 which is pseudo-isocytidine beta-anomer hydrochloride.

4. The compound of claim 1 which is pseudo-isocytidine alpha-anomer and pharmaceutically acceptable acid addition salts thereof.

5. Lower alkyl 2-(2,3-O-lower alkylidene-5-trityl-D-ribofuranosyl)acetate.

6. The compound of claim 5 which is ethyl 2-(2,3-O-isopropylidene-5-O-trityl-D-ribofuranosyl)acetate.

7. Lower alkyl 2-formyl-2-(2,3-O-lower alkylidene-5-O-trityl-D-ribofuranosyl)acetate alkali metal enolate.

8. The compound of claim 7 which is ethyl 2-(2,3-O-isopropylidene-5-O-trityl-D-ribofuranosyl)acetate sodium enolate.

9. Lower alkyl 2-lower alkoxymethylidene-2-(2,3-O-lower alkylidene-5-O-trityl-D-ribofuranosyl)acetate sodium enolate.

10. Ethyl 2-methoxymethylidene-2-(2,3-O-isopropylidene-5-O-trityl-D-ribofuranosyl)acetate.

11. 5-(2,3-O-lower alkylidene-5-O-trityl-D-ribofuranosyl)-isocytosine.

12. The compound of claim 11 which is 5-(2,3-O-isopropylidene-5-O-trityl-D-ribofuranosyl)-isocytosine.

13. A process for the preparation of pseudo-isocytidine which process comprises in combination:

(A) reacting a 2,3-O-lower alkylidene-5-O-trityl-D-ribofuranose with a carbloweralkoxymethylene)-triphenyl phosphorane at elevated temperature to produce lower alkyl 2-(2,3-lower alkylidene-5-O-trityl-D-ribofuranosyl)acetate;

(B) reacting the product from (A) with a lower alkyl formate in the presence of an alkali metal hydride to produce lower alkyl 2-formyl-2-(2,3-O-lower alkylidene-5-O-trityl-D-ribofuranosyl)acetate alkali metal enolate;

(C) reacting the product from (B) with guanidine or an acid addition salt thereof in the presence of a lower alkanolic alkali metal lower alkoxide.

14. The process of claim 13 wherein said alkali metal hydride is sodium hydride, said lower alkanolic alkali metal lower alkoxide is ethanolic sodium ethoxide, said lower alkylidene radical is isopropylidene, said lower alkyl radical is ethyl, said lower alkoxy radical is ethoxy, and said alkali metal enolate is sodium enolate.

15. The process of claim 13 wherein the product from step (B) is reacted with a diazolower alkane to produce a lower alkyl 2-loweralkoxymethylidene-2-(2,3-O-alkylidene-5-O-trityl-D-ribofuranosyl)acetate which is then reacted with guanidine or an acid addition salt thereof in accordance with step (C).

* * * * *